United States Patent [19]

Moren et al.

[11] Patent Number: 5,587,502
[45] Date of Patent: Dec. 24, 1996

[54] HYDROXY FUNCTIONAL ALKOXYSILANE AND ALKOXYSILANE FUNCTIONAL POLYURETHANE MADE THEREFROM

[75] Inventors: Dean M. Moren, North St. Paul, Minn.; Ian R. Owen, River Falls, Wis.

[73] Assignee: Minnesota Mining & Manufacturing Company, St. Paul, Minn.

[21] Appl. No.: 460,349

[22] Filed: Jun. 2, 1995

[51] Int. Cl.$^6$ ............................ C07F 7/10
[52] U.S. Cl. .................. 556/420; 524/588; 524/730; 524/731; 524/858; 524/860; 525/453; 525/458; 525/474; 528/28; 528/29
[58] Field of Search .................. 556/420; 524/588, 524/730, 731, 858, 860; 525/453, 458, 424; 528/28, 29

[56] References Cited

U.S. PATENT DOCUMENTS

| | | | |
|---|---|---|---|
| 4,105,465 | 8/1978 | Berger | 106/308 |
| 4,345,053 | 8/1982 | Rizk et al. | 525/440 |
| 4,822,687 | 4/1989 | Kessel et al. | 428/447 |
| 4,918,200 | 4/1990 | Arkles | 549/214 |
| 5,019,607 | 5/1991 | Coltrain et al. | 523/435 |
| 5,068,304 | 11/1991 | Higachi et al. | 528/28 |
| 5,099,058 | 3/1992 | Sanders et al. | 556/420 X |
| 5,217,805 | 6/1993 | Kessel et al. | 428/352 |
| 5,220,047 | 6/1993 | Pohl et al. | 556/420 |
| 5,266,715 | 11/1993 | Harisiades et al. | 556/420 X |
| 5,384,342 | 1/1995 | Szum | 556/420 X |
| 5,475,124 | 12/1995 | Mazurek et al. | 556/420 X |

FOREIGN PATENT DOCUMENTS

93/20163  10/1993  WIPO .

*Primary Examiner*—Paul F. Shaver
*Attorney, Agent, or Firm*—Gary L. Griswold; Walter N. Kirn; Christine T. O'Shaughnessy

[57] ABSTRACT

The present invention provides a moisture-curable alkoxysilane functional polyurethane prepared from a hydroxy functional alkoxysilane. The hydroxy functional alkoxysilane is a hydroxyalkylenecarbamoylalkylene-alkoxysilanes referred to as a "hydroxycarbamoylsilane". The alkoxysilane functional polyurethanes may be used in a variety of applications to provide, for example, moisture-curable adhesives, sealants, putties and the like.

27 Claims, 2 Drawing Sheets

HYDROXY FUNCTIONAL ALKOXYSILANE AND ALKOXYSILANE FUNCTIONAL POLYURETHANE MADE THEREFROM

FIELD OF THE INVENTION

In general, the present invention relates to hydroxy functional alkoxysilanes and moisture-curable alkoxysilane functional polyurethanes made therefrom. The alkoxysilane functional polyurethanes may be used to provide moisture-curable adhesives, sealants, putties, coatings and the like.

BACKGROUND OF THE INVENTION

Many moisture-curable compositions cure in the presence of moisture to form crosslinked materials. The moisture may be obtained from water vapor in the air or from the substrate to which the moisture-curable composition is applied. Moisture-curable compositions may be used to provide adhesives, sealants, coatings and putties for numerous industries including aerospace and automotive industries. Moisture-curable compositions are advantageous because they do not require heat or solvents to cure.

Moisture-curable composition may comprise, for example, alkoxysilane or isocyanate functional polyurethanes, the alkoxysilane or isocyanate groups providing the active sites for the curing reaction with water. Alkoxysilane functional polyurethanes are preferred over isocyanate functional polyurethanes because they are less toxic, and generally provide better storage and faster cure properties. In addition, isocyanate functional polyurethanes may react with water to form carbon dioxide gas which can cause foaming and a decrease in the strength of the composition.

Numerous methods are known for preparing alkoxysilane functional polyurethane materials. One method, the condensation of an isocyanate functional material with a hydroxy functional alkoxysilane, proceeds as generically illustrated below:

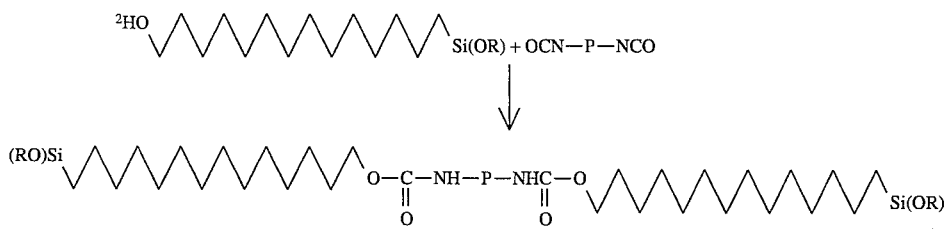

Advantageously, the resulting polyurethane is terminated at both ends with the moisture-reactive alkoxysilane groups to provide optimal curing and enhanced physical properties in the crosslinked material.

One problem with this method, however, is that the hydroxy functional alkoxysilane starting material can undergo an alcohol interchange reaction prior to reaction with the isocyanate functional polymer. For further discussion of alcohol interchange, see *Metal Alkoxides*, D. C. Bradley, R. C. Mehrotra, and D. P. Gaur, Academic Press, New York, 1978. See also Russian Journal Article (Zhurnal Obshchei Khimii Vol. 41, No. 4, page 933, April, 1977) which corroborates the alcohol interchange reaction for hydroxy functional alkoxysilanes having carbamate linkage. The article describes the reaction of ethylene carbonate and aminosilanes to form hydroxyethyl(silylalkyl)carbamates, stating that when ". . . there are alkoxy substituents on the silicon atom, the main reaction is accompanied by processes of inter- and intra-molecular polycondensation with formation of oligomeric products".

The alcohol interchange (i.e., intermolecular polycondensation) reaction is illustrated generically below:

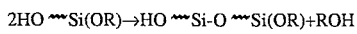

The products formed from the alcohol interchange reaction react with a diisocyanate as follows:

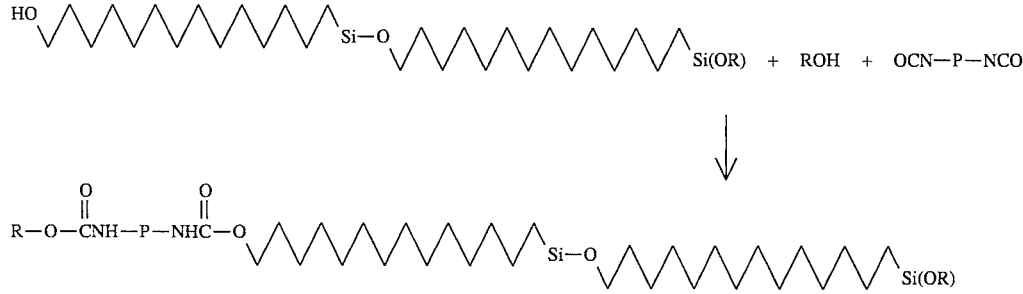

The resulting polyurethane bears an inert terminus (COOR) that does not participate in the crosslinking reaction with moisture. As a consequence, the resulting polyurethane may not sufficiently cure, thus remaining too tacky and providing inadequate strength for some applications.

A need therefore exists for hydroxy functional alkoxysilane materials which are contaminated with minimal amounts of nonlo functional alcohol (ROH). Such materials could be used to provide alkoxysilane functional polyurethanes which overcome the disadvantages associated with isocyanate functional polyurethanes and have good curing and physical properties.

SUMMARY OF THE INVENTION

The present invention provides a novel hydroxy functional alkoxysilane. Preferably, the hydroxy functional alkoxysilane is contaminated with less than 10 mole percent of a non-silane functional alcohol (ROH). More preferably, the hydroxy functional alkoxysilane is contaminated with less than 5 mole percent (most preferably less than 1 mole percent) of a non-silane functional alcohol.

Preferably, the hydroxy functional alkoxysilane compound is a hydroxyalkylenecarbamoylalkylenealkoxysilane (hereinafter referred to as "hydroxycarbamoylsilane") having the following structure:

Structure I

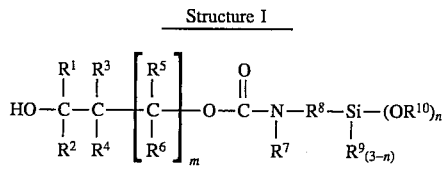

wherein
- each $R^1$, $R^2$, $R^3$, $R^4$, $R^5$, $R^6$ and $R^9$ is independently hydrogen; a linear, branched or cyclic alkyl group having 1 to 18 (preferably 1 to 6) carbon atoms, optionally comprising 1 to 3 non-terminal oxygen, sulfur, nitrogen or carbonyl groups in the hydrocarbon backbone of the alkyl group and optionally substituted with one or more hydroxyl groups; or an aryl group having 6 carbon atoms, optionally substituted with a halo, nitro or cyano group, or an alkyl, alkyloxy, alkylthio, dialkylamino or carboalkyloxy group each having 1 to 18 (preferably 1 to 6) carbon atoms; with the proviso that at least one of $R^1$, $R^2$, $R^3$, and $R^4$ is not hydrogen;
- $R^7$ is hydrogen or a linear, branched or cyclic alkyl group having 1 to 18 (preferably 1 to 6) carbon atoms, optionally comprising 1 to 3 non-terminal oxygen, sulfur, nitrogen or carbonyl groups in the hydrocarbon backbone of the alkyl group;
- $R^8$ is a linear, branched or cyclic alkylene group having at least two (preferably 2 to 10) carbon atoms;
- $R^{10}$ is a linear, branched, or cyclic alkyl group having at least 2 (preferably 2 to 6) carbon atoms, optionally comprising 1 to 3 non-terminal oxygen, sulfur, nitrogen or carbonyl groups in the hydrocarbon backbone of the alkyl group;
- m is 0, 1 or 2; and
- n is 1, 2, or 3.

Preferably, m is 0; one of the $R^1$, $R^2$, $R^3$ and $R^4$ groups is methyl with the remainder of these groups being hydrogen; $R^7$ is hydrogen; $R^8$ is 1,3-propylene; n is 3 and each $R^{10}$ is ethyl. In another preferred embodiment, m is 0; one of the $R^1$, $R^2$, $R^3$ and $R^4$ groups is methyl with the remainder of these groups being hydrogen; $R^7$ is hydrogen; $R^8$ is 1,3-propylene; n is 2; $R^9$ is methyl and each $R^{10}$ is ethyl.

The hydroxycarbamoylsilane may be formed by reaction of a substituted cyclic alkylene carbonate with an aminoalkylenealkoxysilane. The cyclic alkylene carbonate has the following structure:

Structure 2

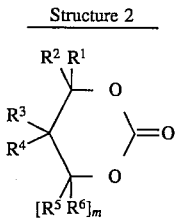

wherein each $R^1$, $R^2$, $R^3$, $R^4$, $R^5$, $R^6$ and m are as described above. The aminoalkylenealkoxysilane has the following structure:

Structure 3

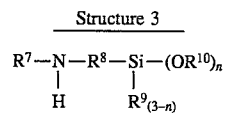

wherein $R^7$, $R^8$, $R^9$, $R^{10}$ and n are also as described above.

In another embodiment, the present invention provides an alkoxysilane functional polyurethane having the structure:

Structure 4

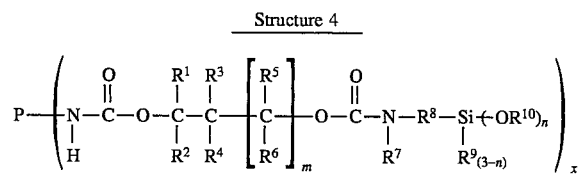

wherein
- each $R^1$, $R^2$, $R^3$, $R^4$, $R^5$, $R^6$ and $R^9$ is independently hydrogen; a linear, branched or cyclic alkyl group having 1 to 18 (preferably 1 to 6) carbon atoms, optionally comprising 1 to 3 non-terminal oxygen, sulfur, nitrogen or carbonyl groups in the hydrocarbon backbone of the alkyl group and optionally substituted with one or more hydroxyl groups; or an aryl group having 6 carbon atoms, optionally substituted with a halo, nitro or cyano group, or an alkyl, alkyloxy, alkylthio, dialkylamino or carboalkyloxy group, each having 1 to 18 (preferably 1 to 6) carbon atoms; $R^7$, $R^8$, $R^{10}$, n and m are as described above; and P is a multivalent organic group. P has valence x wherein x is an integer greater than or equal to 1 (preferably between 2 and 5). Preferably, P has a number average molecular weight between 84 and 12,000, inclusively, more preferably between 5,000 and 10,000, inclusively.

The alkoxysilane functional polyurethane of the present invention is prepared by reaction of an isocyanate functional material having the structure:

Structure 5

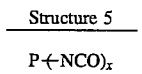

(wherein P and x are as defined above) with a hydroxycarbamoylsilane. Useful hydroxycarbamoylsilanes include those described above as well as those prepared from unsubstituted cyclic alkylene carbonate. By proper selection of P and x, the alkoxysilane functional polyurethane may be tailored to provide a certain viscosity, elongation at break and other physical characteristics that are beneficial for certain applications.

For example, the viscosity of the alkoxysilane functional polyurethane may be increased by increasing the molecular weight of P or by incorporating certain groups (such as dihydrourea groups) into P. Alternatively, the viscosity may be decreased by decreasing the molecular weight of P or by incorporating other groups (such as polyoxyalkylene groups) into P. For example, higher viscosity polyurethanes may be useful to provide moisture curable putties, while lower viscosity polyurethanes may be useful to provide spray adhesives.

The elongation at break of a polyurethane may also be affected by the molecular weight of P as well as the value of x. For example, the elongation at break may increase as the value of x approaches 2 and/or as the molecular weight of P increases. Cured materials having high elongation of break values may be useful to provide sealants which may then be subjected to contraction and expansion.

The nature of the segments comprising P also affects the physical properties of the polyurethane. For example, moisture-curable hot melts are typically provided by employing a P group that comprises a polymer containing high levels of crystalline segments (such as polyhexamethylene adipate). Room temperature applied adhesives, on the other hand, are typically provided by employing a P group comprising amorphous segments (such as polypropylene glycol).

Because of this ability to tailor the alkoxysilane functional polyurethane to achieve different physical properties, it may be used in a wide variety of applications where a moisture-curable material is needed (such as structural, contact, spray and hot melt adhesives, sealants, coatings and putties). Furthermore, the alkoxysilane functional polyurethane of the present invention has good thermal stability and cure characteristics.

DESCRIPTION OF THE INVENTION

Hydroxycarbamoylsilane

Figure 1:
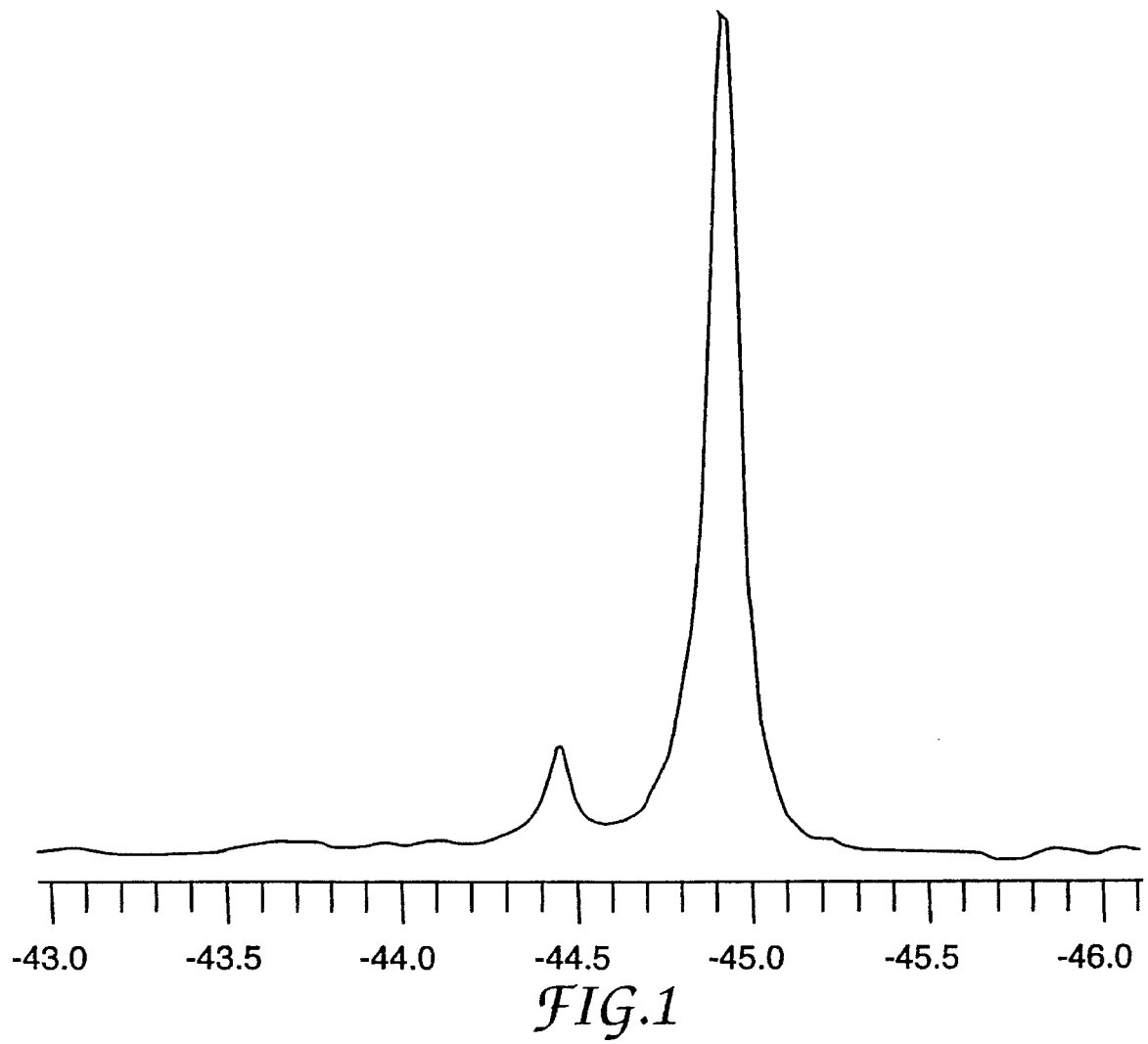
FIG. 1 shows the $^{29}$Si-NMR spectrum of a hydroxycarbamoylsilane of the invention (corresponding to Example 1) which is free from the products of an alcohol interchange reaction. The large peak at $\delta$-44.9 represents the hydroxycarbamoylsilane, while the smaller peak at $\delta$-44.45 represents residual aminoalkylenealkoxysilane used to prepare the hydroxycarbamoylsilane.
Figure 2:
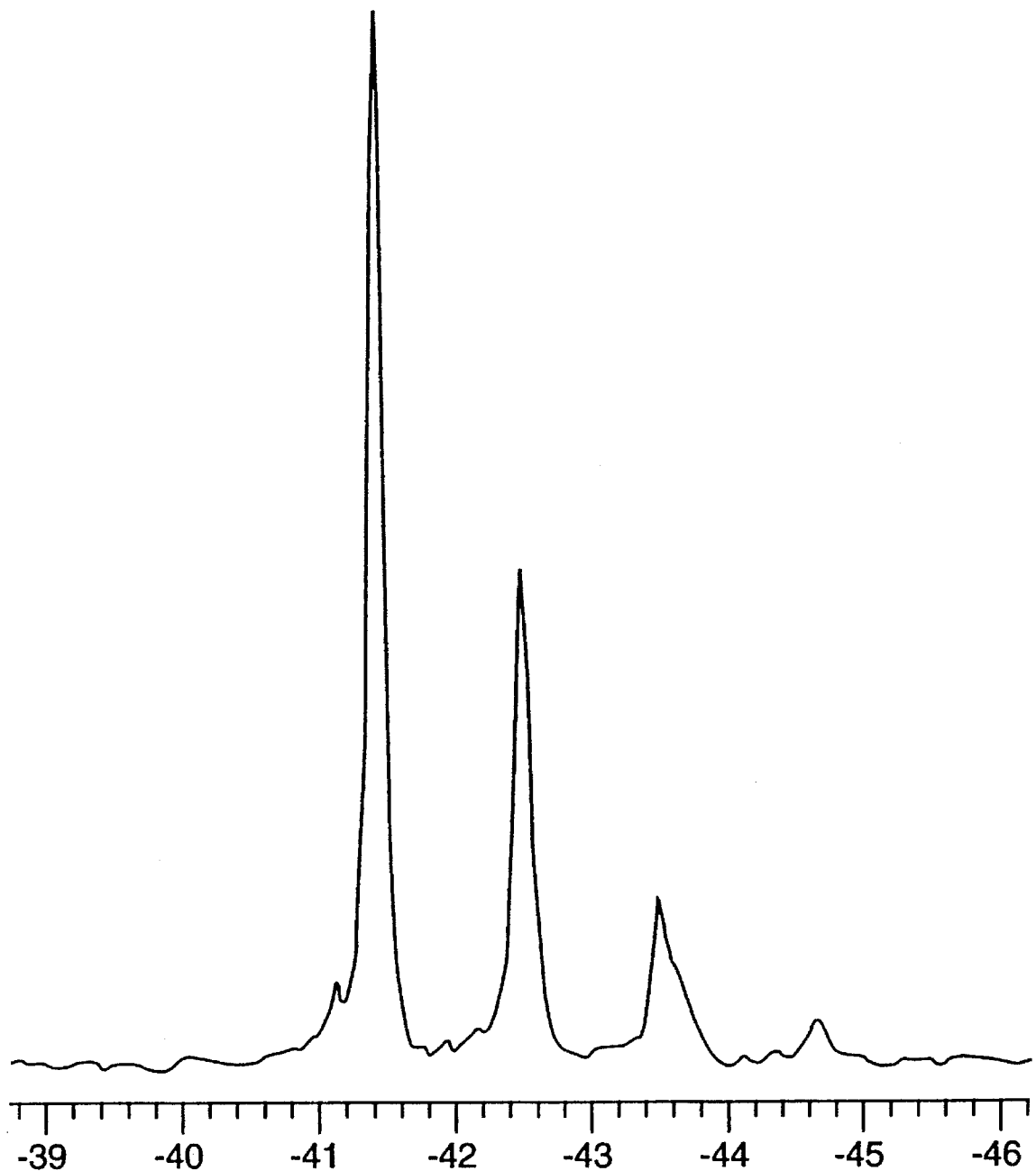
FIG. 2 shows the $^{29}$Si-NMR spectrum of the hydroxycarbamoylsilane of Comparative Example 1 which comprised the products of an alcohol interchange reaction. The large peak at $\delta$-41.4 represents the hydroxycarbamoylsilane, while the smaller peaks at $\delta$-42.5, $\delta$-43.5, and $\delta$-44.6 represent the products of alcohol interchange.

The hydroxycarbamoylsilane of the present invention is obtained by reaction of a substituted cyclic alkylene carbonate with an aminoalkylenealkoxysilane. Useful cyclic alkylene carbonates include 4,5-dimethyl-1,3-dioxolan-2-one, 4,4-dimethyl-1,3-dioxolan-2-one, 4-ethyl-1,3-dioxolan-2-one, 4-methyl-1,3-dioxolan-2-one, and 4-phenoxymethyl-1,3-dioxolan-2-one. The preferred cyclic alkylene carbonate is 4-methyl-1,3-dioxolan-2-one (hereinafter referred to as propylene carbonate or PC).

Useful aminoalkylenealkoxysilanes include 4-aminobutyltriethoxysilane, N-2-(aminoethyl)-3-aminopropyltris(2-ethylhexoxy)silane, 3-aminopropyltris(methoxyethoxyethoxy)silane, 3-aminopropyldimethylethoxysilane, 3-aminopropylmethyldiethoxysilane, 3-aminopropyldiisopropylethoxysilane, 3-aminopropyltriethoxysilane, 3-N-methylaminopropyltriethoxysilane, 3aminopropylphenyldiethoxysilane, 3,3'-aminobis(propyltriethoxysilane), and N-(3-triethoxysilylpropyl)dibutyl spartate. Preferred silanes are 3-aminopropylmethyldiethoxysilane and 3-aminopropyltriethoxysilane.

Preferably, the hydroxycarbamoylsilane is an adduct of propylene carbonate with 3-aminopropylmethyldiethoxysilane or 3aminopropyl triethoxysilane. These preferred hydroxycarbamoylsilanes include:

N-(3-methyldiethoxysilylpropyl)-2-hydroxy-1-propyl carbamate wherein $R^1$ is methyl; $R^2$, $R^3$, and $R^4$ are each hydrogen; m is 0; $R^7$ is hydrogen; $R^8$ is 1,3-propylene; $R^9$ is methyl; $R^{10}$ is ethyl and n is 2 in Structure I;

N-(3-methyldiethoxysilylpropyl)-1-hydroxy-2-propyl carbamate wherein $R^3$ is methyl; $R^1$, $R^2$ and $R^4$ are each hydrogen; m is 0; $R^7$ is hydrogen, $R^8$ is 1,3-propylene; $R^9$ is methyl; $R^{10}$ is ethyl and n is 2 in Structure I;

N-(3-triethoxysilylpropyl)-2-hydroxy-1-propyl carbamate wherein $R^1$ is methyl; $R^2$, $R^3$, and $R^4$ are each hydrogen; m is 0; $R^7$ is hydrogen, $R^8$ is 1,3-propylene; $R^{10}$ is ethyl and n is 3 in Structure I; and N-(3-triethoxysilylpropyl)-1-hydroxy-2-propyl carbamate wherein $R^3$ is methyl; $R^1$, $R^2$ and $R^4$ are each hydrogen; m is 0; $R^7$ is hydrogen, $R^8$ is 1,3-propylene; $R^{10}$ is ethyl and n is 3 in Structure I.

The reaction to produce the hydroxycarbamoylsilane is usually conducted at a temperature ranging from 15°–50° C. Preferably, the reaction is conducted at room temperature (20°–25° C.). Reaction temperatures below room temperature may have a tendency to diminish reaction rates, while reaction temperatures above room temperature may have a tendency to promote degradation of the products via alcohol interchange.

The reaction may be conducted in the absence of solvents; however, if desired, solvents such as acetone, butanone, ethyl acetate, toluene, naphtha, N-methylpyrrolidinone, N,N-dimethylformamide, acetonitrile, tetrahydrofuran, and ethylene glycol dimethyl ether may be employed.

The reaction may be conducted without a catalyst to facilitate the attack of the carbonyl group of cyclic alkylene carbonate. However, if desired, a catalyst such as a tin compound may be employed.

It is usually preferable to carry out the process of the invention with a 1:1 molar ratio of aminoalkylenealkoxysilane to cyclic alkylene carbonate to achieve optimal yields of hydroxycarbamoylsilane. The use of more or less than an equivalent amount of cyclic alkylene carbonate results in mixtures comprising hydroxycarbamoylsilanes with aminoalkylenealkoxysilanes and/or cyclic alkylene carbonates. Although not preferred, these mixtures may be used to form alkoxysilane functional polyurethanes as illustrated in Example 18.

The reaction time required to convert the aminoalkylenealkoxysilane to hydroxycarbamoylsilane will vary widely. Reaction time will depend upon several factors, including the nature of the aminoalkylenealkoxysilane, the substituents on the cyclic alkylene carbonate, the concentration of reactants, and the temperature of the reaction. For example, the reaction of a 1:1 molar ratio of 1,2-propylene carbonate and 3-aminopropyltriethoxysilane was about 90% complete after 18 hours at 22° C. (See Example 1). Progress of the reaction of a aminoalkylenealkoxysilane with a cyclic alkylene carbonate is readily monitored by infrared (IR) spectroscopy by following the disappearance of the carbonate carbonyl stretching frequency near 1800 cm$^{-1}$ and the appearance of the carbamate carbonyl stretching frequency near 1700 cm$^{-1}$.

Once the hydroxycarbamoylsilane has been prepared, it is preferably stored in moisture-free packaging. The presence of moisture can cause hydrolysis of the material, resulting in the formation of non-silane functional alcohol. The hydrolysis reaction may be illustrated generically as follows:

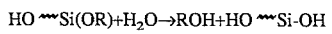

The non-silane functional alcohol (ROH) interferes with the formation of a polyurethane bearing a sufficient number of moisture-reactive alkoxysilane groups.

The presence of competing side reactions, such as alcohol interchange or hydrolysis, may be determined using hydrogen nuclear magnetic resonance spectroscopy ($^1$H-NMR) and silicon magnetic resonance spectroscopy ($^{29}$Si-NMR). The amount of non-silane functional alcohol (if any) present in the hydroxycarbamoylsilane may be determined by ($^1$H-NMR). For example, when the alkoxysilane group is triethoxysilane, the amount of ethanol may be calculated from the integrals of the $^1$H-NMR triplet peaks corresponding to the ethoxysilane methylene ($\delta 3.85$) and the ethanol methylene ($\delta 3.70$).

Using $^{29}$Si-NMR, it is possible to determine the degree of reaction of the aminosilane and the amount of alcohol interchange (if any) that has occurred. A hydroxycarbamoylsilane compound that has not undergone an alcohol interchange reaction will generally exhibit one large peak in the $^{29}$Si-NMR spectrum. A compound that has undergone such a reaction, on the other hand, will exhibit peaks corresponding to the products of the alcohol interchange reaction. For example, N-(3-trimethoxysilylpropyl)-2-hydroxyethyl carbamate exhibits one peak at $\delta$-41.5 when it has not undergone alcohol interchange, while the products of alcohol interchange exhibit additional peaks at about $\delta$-42.4, $\delta$-43.5 and $\delta$-44.6.

Alkoxysilane Functional Polyurethane

The alkoxysilane functional polyurethane of the present invention is prepared by reacting an isocyanate functional material with the hydroxycarbamoylsilane described above or hydroxycarbamoylsilanes prepared from unsubstituted cyclic alkylene carbonate. Preferably, the isocyanate functional material has a number average molecular weight in the range of 90 to 8,000, more preferably 2,000 to 6,000.

Useful isocyanate functional materials include aliphatic, cycloaliphatic, araliphatic, or aromatic isocyanates. Aliphatic isocyanates usually provide adducts having good light stability while aromatic isocyanates are generally more economical. Diisocyanates are preferred. Examples of useful diisocyanates include 2,4-tolylene diisocyanate, 2,6-tolylene diisocyanate, diphenylmethane 4,4'-diisocyanate (hereinafter referred to as MDI), 1,4-phenylene diisocyanate, dicyclohexylmethane diisocyanate (hereinafter referred to as H$_{12}$-MDI), isophorone diisocyanate (hereinafter referred to as IPDI), 1,6-hexanediisocyanate, and 1,3-($\alpha,\alpha$, $\alpha',\alpha'$-tetramethyl)xylylene diisocyanate (hereinafter referred to as TMXDI). Dimers and trimers of the above mentioned isocyanate functional compounds, for example those containing uretadione, biuret, and isocyanurate linkages, are also useful. Preferred diisocyanate functional compounds include IPDI, MDI, and blends of 2,4-tolylene diisocyanate and 2,6-tolylene diisocyanate (hereinafter referred to as TDI).

Other isocyanate functional materials useful in the present invention include those wherein P of Structure 5 is itself a polyurethane. A summary of basic polyurethane chemistry can be found in *Polyurethane: Chemistry and Technology*, Saunders and Frisch, Interscience Publishers (New York, 1963 (Part I) and 1964 (Part II)). Typically, polyurethanes are produced by the condensation reaction of a polyisocyanate and an isocyanate reactive material, i.e., a branched or straight chain polymer or copolymer bearing one or more pendent or terminal isocyanate reactive groups, including hydroxyl, mercaptan, primary or secondary amine, carboxylic acid, epoxy, acetoacetate groups, and the like. The isocyanate reactive material may further bear pendent grafted miscible or immiscible polymer chains or be internally substituted with silicone segments. The isocyanate reactive material may also have a molecular weight less than 200 which is typical for materials known in the art as "chain extenders". Blends of two or more isocyanate reactive materials may also be employed.

Preferred isocyanate reactive materials include those having polyalkylene ester, polyalkylene ether, polyalkylene sulfide, polyalkylene amide, polyalkylene, and polyacrylate backbones. Preferred isocyanate reactive materials also include those with a backbone comprising polypropylene oxide containing very low levels of unsaturation (for example, <0.07 meq vinyl/g polyol). Preparative methods for these materials are known and most are available commercially. Specific examples of useful isocyanate reactive materials include poly(hexamethylene adipate) diol; poly(propylene oxide) diol, diamine, triol, and triamine; polybutadiene diol; poly(butyl acrylate) diol; poly(ethylene oxide)-block-poly(dimethylsiloxane)-block-poly(ethylene oxide) diol; poly(styrene-co-acrylonitrile)-graft-poly(propylene oxide) diol and triol; 2,2-bis(4-(2-hydroxyethoxy)phenyl)propane; 1,4-butanediol; trimethylolpropane and water. Preferred isocyanate reactive materials are poly(propylene oxide) diol and triol and poly(hexamethylene adipate) diol having molecular weights in the range of from 400 to 9000.

Other isocyanate functional materials that may be used to form the alkoxysilane functional polyurethane include organic compounds comprising an average of at least two isocyanate groups per compound without prior chain extension and addition polymers bearing isocyanate groups. Examples of useful addition polymers include copolymers comprising isocyanatoethyl methacrylate, methacryloylisocyanate, and/or 2-(3-isopropenylphenyl)-2-propylisocyanate.

The alkoxysilane functional polyurethane of the present invention may be prepared by condensing an isocyanate functional material with a hydroxycarbamoylsilane using procedures known in the art. Preferably, the molar ratio of NCO equivalents to hydroxycarbamoylsilane is 1:1. Preferably, a stepwise procedure is followed whereby the isocyanate functional material and hydroxycarbamoylsilane are each separately formed and then combined to form the alkoxysilane functional polyurethane.

The condensation reaction to form a polyurethane is typically conducted in the presence of up to 5 % by weight catalyst based on the isocyanate reactive material weight, preferably 0.00005 to 5 wt % catalyst, and more preferably 0.05 to 0.5 wt %. Examples of useful catalysts include those listed in *Polyurethanes: Chemistry and Technology*, Part I, Table 30, Chapter 4, Saunders and Frisch, Interscience Publishers, New York, 1963. Preferred catalysts are the tin IV compounds, for example dibutyltin dilaurate.

Although not preferred because of environmental or energy considerations, the stepwise reactions may optionally be carried out in the presence of solvents. When used, preferred solvents are those which are unreactive with isocyanates and include, for example, ketones, ethers, esters, amides, hydrocarbons, chlorohydrocarbons, and chlorocarbons. Specific examples of preferred solvents include acetone, butanone, ethyl acetate, toluene, naphtha, N-methylpyrrolidinone, N,N-dimethylformamide, acetonitrile, tetrahydrofuran, and ethylene glycol dimethyl ether.

Suitable reaction temperatures are usually between 0° C. and 120° C., preferably between 25° C. and 90° C., more preferably between 50° C. and 80 ° C.

The reaction time required to convert the reactants to the desired alkoxysilane functional polyurethanes will vary widely. Reaction times will depend upon several factors, including the nature of the reactants, the concentration of reactants, and the temperature of the reaction. Progress of the reactions is readily monitored by infrared (IR) spectroscopy by following the disappearance of the isocyanate stretching frequency near 2270 cm$^{-1}$ and the growth of the carbamate carbonyl stretching frequencies near 1700 cm$^{-1}$.

Composite Formulations

Various additives may be used with the alkoxysilane functional polyurethane of the present invention to prepare composite formulations. The additives may be introduced before or during the formation of the alkoxysilane functional polyurethane, provided that the additives are not isocyanate reactive. Alternately, the additives may be introduced after the alkoxysilane functional polyurethane is formed. The additives are usually introduced to perform specific functions. The additives may include, for example, moisture cure catalysts, plasticizers, thixotropes or antisagging agents, antioxidants, biocides, adhesion promoting agents, corrosion inhibitors, fillers (including pigments), colorants, photostabilizers, and perfumes.

Useful moisture cure catalysts include metal salts and complexes, amines, and organic and inorganic acids. Specific examples of useful moisture cure catalysts include dibutyltin diacetylacetonate, tetraisopropyl titanate, calcium oxide, N,N,N',N'-tetramethylguanidine, tetrabutylammonium hydroxide, trifluoroacetic acid, and dibutyl phosphate.

Useful plasticizers include, for example, benzoates, adipates, phthalates, sebacates, and phosphates. The plasticizers may be present at any level, although it is generally preferred that the amount of plasticizer not exceed 50% by weight. Specific examples of useful plasticizers include butyl benzyl phthalate and dipropylene glycol dibenzoate.

Useful thixotropes or antisagging agents include castor waxes, fumed silicas, treated clays, and polyamides. Preferably, the thixotrope is non-reactive with the alkoxysilane groups of the polyurethane to avoid shelf-life problems.

Filler may be added to alter the color, rheology, and ultimate mechanical properties of the alkoxysilane functional polyurethane. Examples of useful fillers include carbon black, calcium carbonate, titanium dioxide, iron oxide, talc, ceramic microspheres and clay. The fillers are preferably free of groups which react with the isocyanate moieties of the isocyanate functional materials or the alkoxysilane moieties of the alkoxysilane functional polyurethane. Stearated, precipitated calcium carbonates are preferred fillers in applications where low cost and opacity are desirable.

Useful adhesion promoters include various silanes such as those available under the tradenames "A1120", "A187", and "A189" from OSI. Useful antioxidants or U.V. stabilizers include those commercially available under the tradenames "TINUVIN 770", "TINUVIN 327", "TINUVIN 1130", and "TINUVIN 292", commercially available from Ciba-Geigy.

The alkoxysilane functional polyurethane of the present invention may be used in moisture curing, one or two part coatings, adhesives, sealants, and elastomers.

The alkoxysilane functional polyurethane is especially useful for providing automotive seam sealers. Automotive seam sealers are typically used in high temperature environments, and as a result, must exhibit thermal stability. In addition, they are typically required to adhere to surfaces such as cold rolled steel, primed steel, and galvanized steel. Furthermore, they are typically required to accept paint shortly after application while still wet, drying to a cured film which shows no defects.

Automotive seam sealers typically comprise additives such as those listed above. When the sealer is used in area of the automobile that will be exposed to high temperatures, a combination of two antioxidants comprising a hindered phenolic antioxidant (such as BHT commercially available from Aldrich) and a hindered amine light stabilizer (such as Tinuvin 770 commercially available from Ciba-Geigy) is preferably used. The weight ratio of hindered amine light stabilizer to hindered phenolic antioxidant is preferably about 1:4.

Preferably, the automobile seam sealer comprises (a) 100 parts by weight of the alkoxysilane functional polyurethane of the invention, (b) 5 to 200 (more preferably 50 to 100) parts by weight of at least one plasticizer, (c) 1 to 10 (more preferably 3 to 8) parts by weight of at least one antioxidant, (d) 0.1 to 5 (more preferably 0.5 to 3) parts by parts by weight of at least one catalyst, (e) 0.1 to 10 (more preferably 3 to 6) parts by weight of at least one adhesion promoter, (f) 0.1 to 10 (more preferably 2 to 4) parts by weight of at least one dehydrator, (g) 0 to 500 (more preferably 250 to 350) parts by weight of at least one filler, and (h) 0 to 20 (more preferably 3 to 8) parts by weight of at least one thixotrope.

The objects and advantages of the instant invention are further illustrated by the following examples, but the particular materials and amounts thereof recited in these examples, as well as other conditions and details, should not be construed to unduly limit this invention. Viscosities were determined at 22° C. using a Brookfield DV-1+viscometer and are reported in Pascal seconds (Pa sec). IR spectra were obtained using a Nicolet 510 FT-IR spectrometer. NMR spectra were obtained using a Varion Unity 500 NMR Spectrometer. The NMR Spectrometer was operated at 500 megahertz to obtain $^1$H-NMR spectra and at 99.325 megahertz with an internal chromium acetylacetonate dopant to obtain the $^{29}$Si-NMR Spectra. All NMR runs were carried out using CDCl$_3$ solvent at 22° C. using standard acquisition parameters. General information regarding the acquisition and interpretation of $^{29}$Si-NMR spectra may be found in *NMR and the Periodic Table*, Chapter 10, Harris and Mann, Academic Press, New York, 1978.

Examples 1–9 and Comparative Example 1 illustrate the preparation of hydroxycarbamoylsilanes. Examples 10–29 and Comparatives 2–6 illustrate the preparation of alkoxysilane functional polyurethanes. Examples 30–55 and Comparative Examples 7–10 illustrate the preparation of composite formulations comprising alkoxysilane functional polyurethanes.

| | Abbreviations |
|---|---|
| HyCS | Blend of hydroxycarbamoylsilanes containing N-(3-triethoxysilylpropyl)-2-hydroxy-1-propyl carbamate and N-(3-triethoxysilylpropyl)-1-hydroxy-2-propyl carbamate |
| PC | Texacar PC, a 1,2-propylene carbonate that is commercially available from Huntsman Company located in Houston, TX |
| A1100 | Silquest A1100, a 3-aminopropyltriethoxysilane that is commercially available from OSi Specialties located in Danbury, CT |
| DS1505 | 3-aminopropylmethyldiethoxysilane commercially available as DS1505 from Hüls located in Piscataway, NJ |
| A1110 | Silquest A1110, a 3-aminopropyltrimethoxysilane that is commercially available from OSi Specialties located in Danbury, CT |
| TDI | Mondur TD-80, an 80:20 blend of 2,4- and 2,6-tolylene diisocyanate that is commercially available from Bayer, Inc. located in Pittsburgh, PA |
| PPG 4025 | Arcol PPG 4025, a 4000 molecular weight polypropylene oxide diol that is commercially available from Arco, Inc. located in Newton Square, PA |
| LHT-28 | Arcol LHT-28, a 6000 molecular weight polypropylene oxide triol available from Arco, Inc. located in Newton Square, PA |
| LHT-28HF | Arcol LHT-28HF, a 6000 molecular weight polypropylene oxide triol having a reported |

-continued

| | Abbreviations |
|---|---|
| | unsaturation level of 0.012 meg vinyl/g polyol available from Arco, Inc. located in Newton Square, PA |
| R1885 | Arcol R1885, a 4000 molecular weight polypropylene oxide diol having a reported unsaturation level of 0.005 meg vinyl/g polyol available from Arco, Inc. located in Newton Square, PA |
| PPG 425 | Arcol PPG 425, a 425 molecular weight polypropylene oxide diol available from Arco, Inc. located in Newton Square, PA |
| PPG 1025 | Arcol PPG 1025, a 1000 molecular weight polypropylene oxide diol available from Arco, Inc. located in Newton Square, PA |
| PPG 2025 | Arcol PPG 2025, a 2000 molecular weight polypropylene oxide diol available from Arco, Inc. located in Newton Square, PA |
| Ultrapflex | a 0.08 micron, precipitated, stearated calcium carbonate available from Specialty Mineral, Adams, MA |
| Benzoflex 9-88 | a dipropylene glycol dibenzoate available from Velsicol, Inc., Rosemont, IL |
| Elftex 8 | carbon black filler available from Cabot, Inc., located in Boston, MA |
| BHT | 2,6-di-tert-butyl-4-methylphenol available from Aldrich Chemical Co., located in Milwaukee, WI |
| DIDP | a di-isodecyl phthlate plasticizer available from Exxon |
| Tinuvin 770 | a light stabilizer available from Ciba-Geigy |
| Vulcan carbon black | carbon black available from Cabot |
| Irganox 1010 | anitoxidant available from Ciba-Geigy |
| Dislon 6500 | polyamide thickener available from King Industries |
| Zeeospheres 600 | ceramic microspheres available from 3M/Zeelan |
| A171 | trimethoxyvinylsilane dehydrator available from OSi Specialties located in Danbury, CT |
| Dabco T-12 or DBDTL | dibutyltindilaurate curing catalyst available from Air Products |
| A1120 | N-beta (aminoethyl) gamma-aminopropyltrimethoxysilane adhesion promoter available from OSi Specialties located in Danbury, CT |
| Neostann U220 | dibutyltin diacetylacetonate curing catalyst available from Kaneka America, located in New York City, NY |
| Isopar H | an aliphatic hydrocarbon solvent available from Exxon |
| EtOH | ethanol |

EXAMPLE 1

Formation Of HyCS

A mixture of 51.05 grams (0.5 moles) PC and 110.69 grams (0.5 moles) A1100 was prepared in a glass jar. The glass jar was capped and shaken, and its contents were allowed to react at 20°–25° C. The degree of reaction was 90% after 18 hours, as determined by the conversion of carbonate peaks to carbamate peaks in the IR spectrum. $^{29}$Si-NMR indicated that the sample was free of the products of alcohol interchange as shown in FIG. 1. FIG. 1 shows a large peak at δ-45 corresponding to HyCS and a smaller peak at δ-44.5 corresponding to unreacted aminosilane. Additionally, the sample exhibited no alcohol interchange even after 30 days at 22° C. in the absence of moisture.

$^1$H-NMR also showed the presence of a non-silane functional alcohol at a level less than 1 mole %.

EXAMPLE 2

Formation of Two Different Blends of Hydroxycarbamoylsilanes

Blend A

A blend of hydroxycarbamoylsilanes comprising N-(3-methyldiethoxysilylpropyl)-2-hydroxy-1-propyl carbamate and N-(3-methyldiethoxysilylpropyl)-1-hydroxy-2-propyl carbamate was prepared.

The same procedure of Example 1 was followed except that the mixture comprised 5.11 grams (0.05 moles) PC and 9.57 grams (0.05 moles) DS1505. The degree of reaction after 18 hours was 92% determined as in Example 1. The $^{29}$Si-NMR indicated that the sample was free of alcohol interchange products.

Blend B

A blend of hydroxycarbamoylsilanes comprising N-(3-triethoxysilylpropyl)-2,3-dihydroxy-1-propyl carbamate and N-(3-triethoxysilylpropyl)-1,3-dihydroxy-2-propyl carbamate was prepared.

The same procedure of Example 1 was followed except that the mixture comprised 5.90 grams (0.05 moles) 3-hydroxy-1,2propylene carbonate (Glyceryl Carbonate available from Huntsman) and 11.05 grams (0.05 mol) A1100. A mild exotherm ensued, raising the reaction temperature to about 40° C. The degree of reaction (determined as in Example 1) was 80% after 0.5 hour and 92% after three days.

EXAMPLES 3 AND 4

Effect Of Reaction Temperature

Two mixtures, each mixture comprising equivalent stoichiometric quantities of PC and A1100 were allowed to react as in Example 1, except that the reaction temperature was increased for each mixture. Sample 3 was allowed to react at 50° C., while Sample 4 was allowed to react at 70° C. The conversion of carbonate to carbamate and the degree alcohol interchange was determined as in Example 1 and is tabulated in Table 1. The mole percent of non-silane functional alcohol (ethanol, EtOH) present in the hydroxycarbamoylsilane was determined using $^1$H-NMR and is reported in Table 1.

TABLE 1

| Ex. | Reaction Temperature | Conversion to Carbamate | Degree of Alcohol Interchange | Mole % EtOH |
|---|---|---|---|---|
| 3 | 50° C. | 89% at 5.25 hours | 0% | 3 |
| 4 | 70° C. | 90% at 3.5 hours | 2.4% | 6 |

This example illustrates that reaction temperatures up to 70° C. promote little alcohol interchange.

EXAMPLES 5–8

Effect of Varying the Molar Ratio of Reactants

Four mixtures of PC and A1100 were combined in various ratios and allowed to react at 20°–25° C. for 18 hours. The molar ratio of the reactants and the molar distribution of the reactants and HyCS in the product are provided in Table 2.

TABLE 2

| Example | Reactant Ratio PC:A1100 | Product Distribution | | |
|---|---|---|---|---|
| | | PC | A1100 | HyCS |
| 5 | 0.8:1.0 | 0 | 20 | 80 |
| 6 | 0.9:1.0 | 1 | 11 | 89 |
| 7 | 1.0:1.0 | 8 | 8 | 92 |
| 8 | 1.5:1.0 | 58 | 8 | 92 |

The results indicate that the product distribution can be controlled by the initial reactant ratios.

EXAMPLE 9A, 9B, 9C

Formation of a Hydroxycarbamoylsilane Using Unsubstituted Cyclic Alkylene Carbonate A hydroxycarbamoylsilane was prepared as in Example 1, except that an unsubstituted cyclic alkylene carbonate was used as a starting reactant and three different reaction temperatures (22° C., 50° C., and 70° C.) were used. In each case, a mixture of 4.15 grams (0.05 moles) 1,3-dioxolan-2-one (ethylene carbonate available from Huntsman) and 11.07 (0.05 moles) A1100 was allowed to react. The conversion of carbonate to carbamate and degree of alcohol interchange were determined as in Example 1 and are reported in Table 2.5. The mole percent of ethanol present in the hydroxycarbamoylsilane was determined using $^1$H-NMR and is reported in Table 2.5.

TABLE 2.5

| Ex. | Reaction Temperature | Conversion to Carbamate | Degree of Alcohol Interchange | Mole % EtOH |
|---|---|---|---|---|
| 9A | 22° C. | 99% after 3 days | 0% | N/M |
| 9B | 50° C. | 97% after 5.0 hours | 0% | 12 |
| 9C | 70° C. | 98% at 3.5 hours | 0% | 18 |

N/M = not measured

None of the samples showed alcohol interchange; however, Examples 9B–9C comprised EtOH. Since the 29Si-NMR indicated the absence of alcohol interchange, the EtOH is believed to be present due to hydrolysis of the material.

A comparison of the data of Table 2.5 with that of Table 1 indicates that hydroxycarbamolysilanes made from unsubstituted cyclic alkylene carbonate comprised greater amounts of EtOH than those prepared from substituted cyclic alkylene carbonate. This suggests that hydroxycarbamoylsilanes made from substituted cyclic alkylene carbonates are less prone to hydrolysis than those made from unsubstituted cyclic alkylene carbonate.

COMPARATIVE EXAMPLE 1

Formation of a Hydroxycarbamoylsilane Using 3-aminopropyltrimethoxysilane

A hydroxycarbamoylsilane was prepared as in Example 1, except that a 3-aminopropyltrimethoxysilane (A1110) was used as a starting reactant. A mixture of 5.11 grams (0.05 moles) PC and 8.96 grams (0.50 moles) A1110 was allowed to react at 22° C. for about 20 hours. The $^{29}$Si-NMR indicated that 46% of the alkoxysilane groups underwent alcohol interchange. This example demonstrates that the use of 3-aminopropyltrimethoxysilane as a starting material results in a hydroxycarbamoylsilane end-product which exhibits high levels of alcohol interchange.

EXAMPLE 10

Preparation of an Alkoxysilane Functional Polyurethane

Part I: Formation Of an Isocyanate Functional Polymer

An isocyanate functional polymer was formed by preparing a homogeneous mixture of the following ingredients:

88.67 grams TDI (1.019 eq. NCO),
1113.69 grams PPG 4025 (0.538 eq OH), and
278.42 grams LHT-28 (0.141 eq. OH).

To this homogeneous mixture, 1.50 grams of DBTDL was added. The atmosphere was inerted with nitrogen, and the mixture was agitated and heated to 70° C. for 18 hours.

Part II: Formation of a Blend of Hydroxycarbamolysilanes

In a separate reactor, a blend of hydroxycarbamolysilanes was prepared using the same procedure described in Example 1.

Part III: Formation of the Alkoxysilane Functional Polyurethane

An alkoxysilane functional polyurethane was prepared by reacting 109.90 grams (0.34 mol) HyCS of Part II with the isocyanate functional polymer of Part I under a nitrogen atmosphere. The mixture was agitated and held at 70° C. After 23 hours, the alkoxysilane functional polyurethane product was allowed to cool. IR indicated complete reaction by the absence of the isocyanate peak (2270 cm$^{-1}$).

EXAMPLES 11–15

Preparation of Alkoxysilane Functional Polyurethanes Using Various Isocyanate Functional Starting Materials The same procedure of Example 10, Part I was repeated five times, except that each time a different organic isocyanate compound was used to prepare the isocyanate functional polymer. The five different organic isocyanate compounds are identified in Table 3. In each case, the quantity of organic isocyanate compound (0.266 equiv. NCO) given in Table 3 was allowed to react with 280 grams of PPG 4025 (0.142 eq OH) and 70 grams of LHT-28 (0.036 eq OH) in the presence of 0.35 grams DBTDL catalyst. The viscosities of the resulting isocyanate functional polymers were measured and can be found in Table 3.

Using the procedure of Example 10, Part III, each of the isocyanate functional polymers (0.009 equiv. NCO) thus obtained was then allowed to react with 2.91 grams (0.009 mol) HyCS prepared as in Example 1. The quantity of isocyanate functional polymer used in each reaction is given in Table 3 along with the viscosities of the resulting alkoxysilane functional polyurethanes.

TABLE 3

| Ex. | Organic Isocyanate Compound | Weight Organic Isocyanate Compound | Isocyanate Functional Polymer Viscosity (Pa sec) | Weight Isocyanate Functional Polymer | Alkoxysilane Functional Polyurethane Viscosity (Pa sec) |
| --- | --- | --- | --- | --- | --- |
| 11 | TDI (Mondur TD-80, Miles) | 23.14 g | 65 | 38.16 g | 240 |
| 12 | MDI (Mondur M, Miles) | 33.25 g | 175 | 39.20 g | 310 |
| 13 | $H_{12}$—MDI (Desmodur W, Miles) | 34.85 g | 115 | 39.36 9 | 280 |
| 14 | TMXDI (TMXDI, Cyanamid, Wayne, NJ) | 32.45 g | 55 | 39.32 9 | 50 |
| 15 | IPDI (Vestanat IPDI, Hüls, Piscataway, NJ) | 29.53 g | 40 | 38.82 g | 100 |

These examples demonstrate that a variety of isocyanate functional polymers may be used to form alkoxysilane functional polyurethanes having different viscosities. This enables the polyurethane to be used in a variety of applications.

EXAMPLES 16–19

Preparation of Alkoxysilane Functional Polyurethanes from HyCS/A1100 Blends

Various blends of HyCS with A1100 were prepared using the same procedure of Example 1 except that the quantities of PC and A1100 were adjusted to provide the molar ratios given in Table 4. More specifically, the amount of PC given in Table 4 was reacted with 11.07 grams (0.05 tool) of A1100. The ratios of carbonate to carbamate in the products were determined by integration of the IR bands at approximately 1800 cm$^{-1}$ and 1700 cm$^{-1}$, respectively. The calculated molar ratio of HyCS:A1100 in the product blends are listed in Table 4.

TABLE 4

| Ex. | Ratio A1100:PC as Charged | Weight (mol) PC | Blend Ratio HyCS:A1100 |
| --- | --- | --- | --- |
| 16 | 100:100 | 5.10 g (0.050) | 92:8 |
| 17 | 100:90 | 4.59 g (0.045) | 89:11 |
| 18 | 100:80 | 4.08 g (0.040) | 80:20 |
| 19 | 100:50 | 2.55 g (0.025) | 50:50 |

Four alkoxysilane functional polyurethanes were prepared using the procedure of Example 10, Part III, by reacting each of the blends described in Table 4 with 34.50 grams (0.008 eq NCO) isocyanate functional polymer prepared as in Example 15. The amount of HyCS:A1100 blend used in the reaction and the viscosities of the resulting alkoxysilane functional polyurethanes are listed in Table 5.

TABLE 5

| Ex. | Product Blend HyCS:A1100 | Weight HyCS:A1100 Blend | Alkoxysilane Functional Polyurethane Viscosity (Pa sec) |
| --- | --- | --- | --- |
| 16 | 92:8 | 2.58 g | 120 |
| 17 | 89:11 | 2.50 g | 130 |
| 18 | 80:20 | 2.42 g | 150 |
| 19 | 50:50 | 2.18 g | 220 |

These examples demonstrate that blends of hydroxycarbamolysilanes with aminoalkylenealkoxysilanes may be used as starting materials for the preparation of alkoxysilane functional polyurethanes.

EXAMPLE 20

Preparation of an Alkoxysilane Functional Polyurethane from Isocyanate Functional Polymer having Low Level of Unsaturation An isocyanate functional polymer having a low unsaturation level was formed by preparing a homogeneous mixture of the following ingredients:

27.37 grams (0.274 eq NCO) IPDI as described in Example 15, 70 grams (0.034 eq OH) of LHT-28HF from Arco, Inc., and 280 grams (0.130 eq OH) of R1885, from Arco, Inc.

To this homogeneous mixture, 0.35 grams of DBTDL was added. The atmosphere was inerted with nitrogen, and the mixture was agitated and heated to 70° C. The Brookfield viscosity of the resulting isocyanate functional polymer was 75 Pa sec.

16.15 grams (0.05 mol) HyCS, prepared as in Example 1, was allowed to react with 227.5 grams of the isocyanate functional polymer described above using the same procedure described in Example 10, Part III. The Brookfield viscosity of the resulting alkoxysilane functional polyurethane was 180 Pa sec. This example demonstrates that alkoxysilane functional polyurethanes may be prepared from an isocyanate functional polymer based on polyols having low levels of unsaturation.

EXAMPLE 21

Preparation of an Alkoxysilane Functional Polyurethane from a Blend of Hydroxycarbamoylsilanes Blend A (0.009 mol) prepared in Example 2 was reacted with 38.82 grams (0.009 eq NCO) of an isocyanate functional polymer prepared as in Example 15, using the same procedure given in Example 10, Part III, to form an alkoxysilane functional polyurethane.

EXAMPLE 22

Preparation of Alkoxysilane Functional Polyurethane Comprising Segments Derived from 1,4-Butanediol An isocyanate functional polymer was formed by preparing a homogeneous mixture of the following ingredients:

30.72 grams (0.004 eq OH) PPG 4025,
7.68 grams (0.004 eq OH) LHT-28,
5.66 grams (0.065 eq NCO) TDI and
1.60 grams (0.036 eq OH) 1,4-butanediol (available from BASF located in Parsippany, N.J.).

To this homogeneous mixture, 0.04 grams of DBDTL was added to form the isocyanate functional polymer using the same procedure of Example 10, Part 1.

3.47 grams (0.01 mol) of HyCS, prepared as in Example 1, and 8 grams of N-methylpyrrolidinone (available from Mallinckrodt located in Paris, Ky.) were added to the isocyanate functional polymer under nitrogen atmosphere. The N-methylpyrrolidinone was added to reduce the viscosity of the mixture. The mixture was agitated and held at 70° C. for 18 hours and found to have a Brookfield viscosity of 160 Pa sec.

EXAMPLES 23–26

Preparation of Alkoxysilane Functional Polyurethane Comprising Segments Derived from Polyols with Various Molecular Weights Four different isocyanate functional polymers were prepared using three different polypropylene oxide diols (referred to in Table 6 as Polyols), each having a different molecular weight. The three polypropylene oxide diols were PPG 425, PPG 1025, PPG 2025 (reported to have approximate molecular weights of 425, 1000 and 2000, respectively). The general procedure as described in Example 10, Part I was used to prepare the isocyanate functional polymers. The quantities of each component (Polyol, PPG 4025 and IPDI) are listed in Table 6. In each case, DBTDL (0.08 grams) was used to catalyze the condensation. The isocyanate functional polymers were reacted with HyCS, prepared as in Example 1, using the same procedure of Example 10, Part III. The quantity of HyCS used in each reaction is given in Table 6.

TABLE 6

| Ex. | Polyol | Weight Polyol (equiv. OH) | Weight PPG 4025 (equiv. OH) | Weight IPDI (equiv. NCO) | Weight HyCS (mol) |
|---|---|---|---|---|---|
| 23 | PPG 425 | 5 g (0.023) | 35 g (0.017) | 5.52 g (0.050) | 3.06 g (0.010) |
| 24 | PPG 1025 | 10 g (0.020) | 30 g (0.015) | 4.95 g (0.045) | 3.20 g (0.010) |
| 25 | PPG 2025 | 10 g (0.010) | 30 g (0.015) | 3.81 g (0.034) | 3.17 g (0.010) |
| 26 | PPG 2025 | 40 g (0.040) | none | 5.55 g (0.050) | 3.23 g (0.010) |

These examples show that alkoxysilane functional polyurethanes may be derived from polyols having different molecular weights,

EXAMPLES 27–29

Preparation of Alkoxysilane Functional Polyurethanes Prepared From Isocyanate Functional Polymers Having Different Molecular Weights A set of isocyanate functional polymers having different molecular weights was prepared by combining the quantity of IPDI listed in Table 7 with 40 grams (0.019 eq OH) of PPG 4025 to form a homogeneous mixture. To this homogeneous mixture, 0.08 grams of DBTDL was added. The atmosphere was inerted with nitrogen, and the mixture was agitated and heated to 70° C. to form an isocyanate functional polymer. The resulting isocyanate functional polymers were subsequently converted to a corresponding set of alkoxysilane functional polyurethanes, following the procedure of Example 10, Part III. The quantities of HyCS used and the viscosity of the resulting alkoxysilane functional polyurethanes are given in Table 7.

TABLE 7

| Ex. | NCO:OH Ratio | Weight IPDI (equiv. NCO) | Weight HyCS (mol) | Brookfield Viscosity |
|---|---|---|---|---|
| 27 | 1.5:1 | 3.21 g (0.029) | 3.13 g (0.010) | 100 |
| 28 | 1.75:1 | 3.75 g (0.034) | 4.68 g (0.015) | 50 |
| 29 | 2:1 | 4.28 g (0.039) | 6.23 g (0.019) | 40 |

These examples demonstrate that alkoxysilane functional polyurethanes may be derived from isocyanate polymers having different molecular weights to achieve different end-product viscosities.

COMPARATIVE EXAMPLES 2–6

Alkoxysilane Functional Polyurethane Prepared from an Amine Functional Alkoxysilane.

Each of the isocyanates (0.009 eq NCO) of Examples 11–15 (TDI, MDI, $H_{12}$-MDI, TMXDI, and IPDI) was allowed to react with 1.99 grams (0.009 mol) A1100 (in place of HyCS) using the same procedure of Example 10, Part III. The quantity of each of the isocyanate functional polymers used in these reactions was the same as that used in the reactions of Examples 11–15 and may be located in the fifth column of Table 3. Table 8 provides the viscosities of the alkoxysilane functional polyurethanes based on the amine functional alkoxysilane. A comparison of the viscosities of Table 3 with those of Table 8 indicates that lower viscosities are achieved with the present invention. This is important in providing materials that may be used in a variety of applications where lower viscosity is preferred.

TABLE 8

| Comparative Example | Organic Isocyanate Compound | Alkoxysilane Functional Polyurethane Viscosity |
|---|---|---|
| 2 | TDI | 900 |
| 3 | MDI | 450 |
| 4 | H$_{12}$—MDI | 610 |
| 5 | TMXDI | 110 |
| 6 | IPDI | 160 |

EXAMPLES 30–48

Preparation of Composite Materials

Creamy dispersions of the following ingredients were made using a 42 mm diameter, saw tooth, dispersing blade (available from Premier Mill located in Reading, Pa.):

36 grams of Ultraflex;

8 grams of Benzoflex 9-88; and 36 grams of an alkoxysilane functional polyurethane chosen from those prepared in Examples 11–29.

The creamy dispersions were allowed to cool and the Brookfield viscosities were measured. 0.36 grams of Neostann U220 was added to each dispersion. The dispersions were degassed under vacuum (approximately 1 mm Hg) at ambient temperature and were spread against polytetrafluoroethylene surfaces in the form of films approximately 1 mm thick. The films were allowed to cure for seven days at 25° C. and 50% relative humidity. The tensile strength at break, elongation at break, and ultimate tear strength were measured for each cured film according to ASTM D412 and D624. The results are given in Table 9.

EXAMPLE 49

Preparation of a Composite Material

The general procedure of Examples 30–48 was repeated, except that:

(1) 60 grams of the alkoxysilane functional polyurethane of Example 15, (2) 12 grams of the Benzoflex 9-88, (3) 0.60 grams of Neostann U220, and (4) 8.8 grams of Elftex 8 carbon black filler were combined to form a creamy dispersion.

The viscosity of the dispersion was 1,700 Pa sec and the cured film had a tensile strength at break of 3700 kPa, elongation at break of 380%, and 5 kN/m tear strength.

EXAMPLES 50–53

Preparation of Composite Materials

The general procedure of Examples 30–48 was repeated using only the alkoxysilane functional polyurethane of Example 15 and varying amounts of alkoxysilane functional polyurethane, Ultraflex and Neostann U220. The ingredient weights and the resulting properties are shown in Table 10.

TABLE 9

| Ex. | Alkoxysilane Functional Polyurethane | Formulation Viscosity (Pa sec) | Tensile Strength (kPa) | Elongation (%) | Tear Strength (kN/m) |
|---|---|---|---|---|---|
| 30 | Example 11 | 530 | 5400 | 490 | 16 |
| 31 | Example 12 | 1,750 | 3800 | 340 | 12 |
| 32 | Example 13 | 1,140 | 4800 | 420 | 14 |
| 33 | Example 14 | 280 | 3900 | 510 | 12 |
| 34 | Example 15 | 490 | 5200 | 480 | 16 |
| 35 | Example 16 | 510 | 5000 | 470 | 14 |
| 36 | Example 17 | 570 | 5000 | 500 | 16 |
| 37 | Example 18 | 590 | 5200 | 500 | 16 |
| 38 | Example 19 | 950 | 4900 | 460 | 14 |
| 39 | Example 20 | 1,000 | 4800 | 290 | 16 |
| 40 | Example 21 | 860 | 5900 | 730 | 18 |
| 41 | Example 22 | 1,150 | 4900 | 480 | 19 |
| 42 | Example 23 | 2,250 | 3700 | 700 | 18 |
| 43 | Example 24 | 1,380 | 4000 | 730 | 16 |
| 44 | Example 25 | 660 | 5200 | 590 | 16 |
| 45 | Example 26 | 1,330 | 4200 | 410 | 14 |
| 46 | Example 27 | 285 | 4300 | 510 | 12 |
| 47 | Example 28 | 200 | 3900 | 350 | 11 |
| 48 | Example 29 | 220 | 4400 | 270 | 11 |

These examples demonstrate that the alkoxysilane functional polyurethane of the present invention may be formulated to provide composites having various beneficial physical properties.

TABLE 10

| Ex. | Weight Polymer | Weight Ultraflex | Weight Niax U220 | Formulation Viscosity (Pa s) | Tensile Strength (kPa) | Elongation (%) | Tear Strength (kN/m) |
|---|---|---|---|---|---|---|---|
| 50 | 44 g | 28 g | 0.44 g | 200 | 3800 | 330 | 11 |
| 51 | 40 g | 32 g | 0.40 g | 280 | 3800 | 340 | 12 |
| 52 | 32 g | 40 g | 0.32 g | 2,250 | 5000 | 400 | 14 |
| 53 | 28 g | 44 g | 0.28 g | 3,560 | 5000 | 370 | 18 |

These examples demonstrate that various physical properties may be achieved by modifying the composite formulation.

EXAMPLE 54

Thermal Stability of a Composite Material

The general procedure of Examples 30–48 was repeated, except that an antioxidant was incorporated into the moisture curable material. A dispersion was prepared by adding 144 grams Ultraflex to a homogenous blend of 25.6 grams Benzoflex 9-88 and 144 grams of an alkoxysilane functional polyurethane prepared as in Example 15. A solution containing 0.11 grams BHT and 0.50 grams Benzoflex 9-88 was added to 25.4 grams of the dispersion. Neostann U220 (0.11 grams) was added, and the moisture curable material was poured into an aluminum dish to a depth of 8 mm. The sample was allowed to cure at 25° C. and 50% relative humidity for 18 hours and then was held at 85° C. and 15% relative humidity for 16 days. The material remained elastomeric and retained a smooth, glossy, tack-free surface, thus demonstrating good thermal stability and cure characteristics.

COMPARATIVE EXAMPLES 7–9

The same composites of Examples 30–34 were prepared except for the use of the alkoxysilane functional polyurethanes of Comparative Examples 2–6, respectively, in place of those listed in Table 9. The composites prepared from the alkoxysilane functional polyurethanes of Comparative Examples 2 and 4 were too viscous to evaluate effectively, and therefore no data is presented for these samples in Table 11.

TABLE 11

| Comparative Ex. | Alkoxysilane Functional Polyurethane | Formulation Viscosity (Pa sec) | Tensile Strength (kPa) | Elongation (%) | Tear Strength (kN/m) |
|---|---|---|---|---|---|
| 7 (MDI) | Comparative Example 3 | 2,200 | 3900 | 280 | 16 |
| 8 (TMXDI) | Comparative Example 5 | 540 | 4100 | 460 | 11 |
| 9 (IPDI) | Comparative Example 6 | 870 | 4100 | 250 | 14 |

An overall comparison of the physical properties of Comparative Examples 7–9 with those of Examples 30–34, respectively, shows that in general, lower viscosities were achieved with the examples of the present invention. This is important if the alkoxysilane functional polyurethane is to be used in applications requiring a low viscosity material such as spray adhesive applications. The overall elongation at break values for Examples 31, 33 and 34 were higher than those of Comparative Examples 7–9.

COMPARATIVE EXAMPLE 10

The same composite of Example 30 was prepared, except for the use of a HyCS of Example 1 which was forced to undergo alcohol interchange by heating to 110° C. for 22 hours. $^{29}$Si-NMR and $^1$H-NMR indicated that the HyCS was contaminated with 16 mole percent EtOH, 10 mole percent from an alcohol interchange reaction. The composite had a viscosity of 565 Pa sec. A tacky product resulted from attempts to cure the composite by exposure to ambient conditions for one week at 20°–25° C. The resulting material had a tensile strength of 1900 kPa, an elongation of 480% and a tear strength of 1 kN/m. A comparison of this data with that of Example 30 (in which HyCS of Example 1 showing no alcohol interchange was used) demonstrates the advantages of the present invention. More specifically, the composite of Example 30 had a viscosity of 530 Pa sec, a tensile strength of 5400 kPa, an elongation of 490% and a tear strength of 16 kN/m. Thus, the composite prepared from the HyCS had a higher tensile and tear strength than one prepared from HyCS that was contaminated with 16 mole percent EtOH.

EXAMPLE 55

Preparation of an Automotive Seam Sealer

A composite material for sealing automobile body seams was prepared in this example. Seam sealers are frequently used in the automotive industry to cover the interface formed by two overlapping pieces of metal. The seam sealer provides corrosion resistance to and improves the aesthetic appearance of the overlap area.

A 4 gallon high shear Myers mixer was flushed with nitrogen and filled with the following components:

2000 grams of the polyurethane of Example 15, 1000 grams DIDP plasticizer, 20 grams Tinuvin 770 antioxidant, 80 grams Irganox 1010 antioxidant, 1 gram Vulcan carbon black, and 100 grams DisIon 6500 thickener.

The components were mixed at high speed for 5 minutes while under a nitrogen blanket. To this, 500 grams of Ultraflex (previously dried overnight at 104° C. (220° F.)) were added and mixed at high speed under nitrogen for 20 minutes while heating the mixture to 77°–82° C. (170°–180° F.). To this, 5300 grams of Zeeospheres 600 ( (previously dried overnight at 104° C. (220° F.)) were added and mixed at high speed under nitrogen for 45 minutes while heating the mixture to 77°–82° C. (170°–180° F.). The mixture was then cooled to 49°–54° C. (120°–130° F.), and the following components were then added: 60 grams of A171 dehydrator, 2 grams of Dabco T-12 dehydrator accelerator, and 240 grams of Isopar H solvent. This was mixed at high speed for 60 minutes under nitrogen at 49°–54° C. (120°–130° F.). To this, 120 grams of A1120 adhesion promoter and 20 grams Neostann U220 curing catalyst dissolved in 240 grams Isopar H solvent were added and mixed at high speed for 15 minutes under nitrogen at 49°–54° C. (120°–130° F.). A vacuum was pulled on the resulting mixture to remove all nitrogen bubbles. The mixture was then immediately stored in aluminum or thick walled high density polyethylene cartridges.

The seam sealer was tested for tack free time, hardness, adhesion, wet-on-wet paintability and shelf-life using the following test procedures:

Tack Free Time

This test was performed in a controlled environment having a temperature of 21° C. (70° F.) and a relative humidity of 50%. A 0.64 cm (0.25 in) bead of seam sealer was applied to a surface. Tack free time was recorded as the amount of time required before the surface of the sealer could be lightly touched by fingertip without transfer to the finger.

Hardness

This test was performed in a controlled environment having a temperature of 21° C. (70° F.) and a relative humidity of 50%. A 0.64 cm (0.25 in) bead of seam sealer was applied to a surface. Six to seven measurements were taken on the bead using a Shore A Hardness Indentor after the bead had been allowed to sit for 24 hours (initial reading) and seven days (final reading). Results are reported as an average of the six to seven measurements.

Adhesion

A 0.64 cm (0.25 in) diameter, 22.9 cm (9 in) long bead of seam sealer was applied to a cold rolled steel panel (30.5 cm (12 in)×10.16 (4 in)) that had been cleaned by wiping first with methyl ethyl ketone, then with toluene, and then again with methyl ethyl ketone. The bead was allowed to cure for one week in a controlled environment having a temperature of 21° C. (70° F.) and a relative humidity of 50%. One end of the bead was cut away from the steel panel to form a free end. The free end was pulled, and the failure mode of the sealer was noted. Cohesive failure occurred when the sealer split apart, leaving sealer residue on the panel. Adhesive failure occurred when the sealer lifted off the panel, leaving no residue. Of these two modes of failure, cohesive failure is preferred.

Cold Flexibility

A panel bearing a bead of cured sealer was prepared as described above for the adhesion test. The panel was placed in a –20° C. (–4° F.) refrigerator for one hour. The panel was then bent 180 degrees over a 2.54 cm (1 in) diameter rod. The sealer failed this test if it pulled away from the panel without leaving any residue (i.e., adhesive failure) or if it showed any cracks at the point of bending.

Wet-On-Wet Paintability

A 0.64 cm (0.25 in) diameter, 22.9 cm (9 in) long bead of seam sealer was applied to a cold rolled steel panel (30.5 cm (12 in)×10.16 (4 in)) that had been cleaned by wiping first with methyl ethyl ketone, then with toluene, and then again with methyl ethyl ketone. The bead was then smoothed to form a 0.16 cm (0.063 in) thick film. Paint (PPG Deltron base clear available from Pittsburgh Paint & Glass, Inc. located in Strongsville, Ohio) was then applied to the film immediately after application in one case and after 60 minutes in another case. The painting sequence was per the manufacturer instructions: One part base coat was mixed with 1.5 parts reducer. Two applications of base coat were applied ten minutes apart using a spray pressure of 45 psi. A minimum of twenty minutes later, three coatings of the clear coat (comprising 2 parts clear, 1 part hardener, and 1 part reducer) were applied to the base coat ten minutes apart using a spray pressure of 45 psi. The paint surface was checked for the presence of cracking, wrinkling of the paint film, or shrinkage at the edges of the painted sealer. After three days, the painted samples were examined to determine whether the paint and sealer had properly cured. Proper paint cure was indicated by a dry paint surface. Proper sealer cure was determined by cutting the sealer and examining whether it was dry throughout. If no defects were seen using the various inspection procedures, the sealer was considered to have wet-on-wet paintability.

Shelf Life

A cartridge of sealer was tested for tack free time, hardness, adhesion, cold flexibility, and viscosity and then stored in a 120° F. oven for four weeks. The sealer was then re-tested. If no significant change in the test results were observed and if the sealer showed no product separation after aging, then the sealer was considered to have good shelf life. Cartridges used for aging comprise either aluminum or high density polyethylene.

The seam sealer of this example gave a tack free time of 22 minutes, an initial hardness of 29, a final hardness of 46, and cohesive failure in the adhesion test. The seam sealer also passed the cold flexibility test and provided wet-on-wet paintability and good shelf life.

We claim:

1. A compound having the structure:

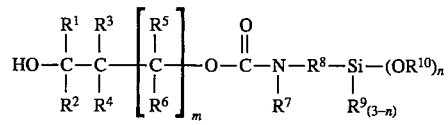

wherein each $R^1$, $R^2$, $R^3$, $R^4$, $R^5$, $R^6$ and $R^9$ is independently selected from the group consisting of hydrogen; linear, branched and cyclic alkyl groups having 1 to 18 carbon atoms, optionally comprising 1 to 3 non-terminal oxygen, sulfur, nitrogen or carbonyl groups in the hydrocarbon backbone of the alkyl group and optionally substituted with one or more hydroxyl groups; and aryl groups having 6 carbon atoms, optionally substituted with a halo, nitro or cyano group, or an alkyl, alkyloxy, alkylthio, dialkylamino or carboalkyloxy group each having 1 to 18 carbon atoms; with the proviso that at least one of $R^1$, $R^2$, $R^3$ and $R^4$ is not hydrogen;

$R^7$ is selected from the group consisting of hydrogen and linear, branched and cyclic alkyl groups having 1 to 18 carbon atoms, optionally comprising 1 to 3 non-terminal oxygen, sulfur, nitrogen or carbonyl groups in the hydrocarbon backbone of the alkyl group;

$R^8$ is selected from the group consisting of linear, branched and cyclic alkylene groups having at least two carbon atoms;

$R^{10}$ is selected from the group consisting of linear, branched, and cyclic alkyl groups having at least 2 carbon atoms, optionally comprising 1 to 3 non-terminal oxygen, sulfur, nitrogen or carbonyl groups in the hydrocarbon backbone of the alkyl groups; m is 0, 1 or 2; and n is 1, 2, or 3.

2. A compound according to claim 1 wherein each $R^1$, $R^2$, $R^3$, $R^4$, and $R^9$ is selected from 1059 the group consisting of hydrogen and linear, branched and cyclic alkyl groups having 1 to 6 carbon atoms; $R^7$ is selected from the group consisting of hydrogen and linear, branched and cyclic alkyl groups having 1 to 6 carbon atoms; $R^8$ is selected from the group consisting of linear, branched and cyclic alkylene groups having 2 to 10 carbon atoms; $R^{10}$ is selected from the group consisting of linear, branched, and cyclic alkyl groups having 2 to 6 carbon atoms; m is 0; and n is 2 or 3.

3. A compound according to claim 2 wherein m is 0; one of the $R^1$, $R^2$, $R^3$ or $R^4$ groups is methyl with the remainder of these groups being hydrogen; $R^7$ is hydrogen; and $R^8$ is 1,3-propylene.

4. A compound according to claim 3 wherein n is 3 and each $R^{10}$ is ethyl.

5. A compound according to claim 3 wherein n is 2 and $R^9$ is methyl and each $R^{10}$ is ethyl.

6. A compound according to claim 1 made by reacting a cyclic alkylene carbonate with an aminoalkylenealkoxysilane.

7. A compound according to claim 6 made by reacting a 0.5:1 to 1:0.5 molar ratio of said cyclic alkylene carbonate to said aminoalkylenealkoxysilane.

8. A compound according to claim 6, wherein said reaction is conducted at a temperature of between 10° and 70° C.

9. A compound according to claim 6, wherein said reaction is conducted at a temperature of between 20° and 25° C.

10. A compound according to claim 1 contaminated with less than 10 mole percent of a non-silane functional alcohol.

11. A compound according to claim 1 contaminated with less than about 5 mole percent of a non-silane functional alcohol.

12. A compound according to claim 1 contaminated with less than about 1 mole percent of a non-silane functional alcohol.

13. An alkoxysilane functional polyurethane having the structure:

$$\left( P \begin{array}{c} \\ \end{array} \underset{H}{\overset{O}{\underset{\|}{N-C}}} - O - \underset{R^2}{\overset{R^1}{\underset{|}{C}}} - \underset{R^4}{\overset{R^3}{\underset{|}{C}}} \left[ \underset{R^6}{\overset{R^5}{\underset{|}{C}}} \right]_m - O - \underset{R^7}{\overset{O}{\underset{\|}{C-N}}} - R^8 - Si \epsilon OR^{10})_n \underset{R^{9}{(3-n)}}{} \right)_x$$

wherein each $R^1$, $R^2$, $R^3$, $R^4$, $R^5$, $R^6$ and $R^9$ is independently selected from the group consisting of hydrogen; linear, branched and cyclic alkyl groups having 1 to 18 carbon atoms, optionally comprising 1 to 3 non-terminal oxygen, sulfur, nitrogen or carbonyl groups in the hydrocarbon backbone of the alkyl group and optionally substituted with one or more hydroxyl groups; and aryl groups having 6 carbon atoms, optionally substituted with a halo, nitro or cyano group, or an alkyl, alkyloxy, alkylthio, dialkylamino or carboalkyloxy group, each having 1 to 18 carbon atoms;

$R^7$ is selected from the group consisting of hydrogen and linear, branched and cyclic alkyl groups having 1 to 18 carbon atoms, optionally comprising 1 to 3 non-terminal oxygen, sulfur, nitrogen or carbonyl groups in the hydrocarbon backbone of the alkyl group;

$R^8$ is selected from the group consisting of a linear, branched and cyclic alkylene groups having at least two carbon atoms;

$R^{10}$ is selected from the group consisting of a linear, branched, and cyclic alkyl groups having at least 2 carbon atoms, optionally comprising 1 to 3 non-terminal oxygen, sulfur, nitrogen or carbonyl groups in the hydrocarbon backbone of the alkyl group;

m is 0, 1 or 2;

n is 1, 2, or 3; and

P is an organic group having valence x, wherein x is an integer greater than or equal to 1.

14. An alkoxysilane functional polyurethane according to claim 13 wherein m is 0; one of the $R^1$, $R^2$, $R^3$, or $R^4$ groups is methyl with the remainder of these groups being hydrogen; $R^7$ is hydrogen; $R^8$ is 1,3-propylene.

15. An alkoxysilane functional polyurethane according to claim 14 wherein n is 3 and each $R^{10}$ is ethyl.

16. An alkoxysilane functional polyurethane according to claim 14 wherein n is 2 and $R^9$ is methyl and each $R^{10}$ is ethyl.

17. An alkoxysilane functional polyurethane according to claim 13 comprising the reaction product of an isocyanate functional material and a hydroxy functional alkoxysilane.

18. An alkoxysilane functional polyurethane according to claim 13 wherein said P comprises a multivalent organic group having a molecular weight in the range of from about 84 to about 12,000.

19. An alkoxysilane functional polyurethane according to claim 13 wherein said P comprises a multivalent organic group having a molecular weight in the range of from about 5,000 to about 10,000.

20. An alkoxysilane functional polyurethane according to claim 13 wherein said P comprises a polyurethane backbone prepared by reacting an isocyanate reactive material with a polyisocyanate.

21. An alkoxysilane functional polyurethane according to claim 20 wherein said isocyanate reactive material is selected from the group consisting of poly(propylene oxide) diol and triol, and poly(hexamethylene adipate) diol.

22. An alkoxysilane functional polyurethane according to claim 20 wherein said isocyanate reactive material has a molecular weight in the range of from 90 to 8,000.

23. An alkoxysilane functional polyurethane according to claim 20 wherein said isocyanate reactive material has a molecular weight in the range of from 2,000 to 6,000.

24. An alkoxysilane functional polyurethane according to claim 20 wherein said polyisocyanate is selected from the group consisting of isophorone diisocyanate and blends of 2,4-tolylene diisocyanate and 2,6-tolylene diisocyanate.

25. A composite formulation comprising the alkoxysilane functional polyurethane of claim 13.

26. A composite formulation according to claim 25 comprising at least one additive selected from the group consisting of antioxidant, plasticizer, curing catalyst and filler.

27. An automobile seam sealer comprising:

(a) 100 parts by weight of the alkoxysilane functional polyurethane of claim 13, (b) 5 to 200 parts by weight of at least one plasticizer, (c) 1 to 10 parts by weight of at least one antioxidant, (d) 0.1 to 5 parts by parts by weight of at least one catalyst, (e) 0.1 to 10 parts by weight of at least one adhesion promoter, (f) 0.1 to 10 parts by weight of at least one dehydrator, (g) 0 to 500 parts by weight of at least one filler, and (h) 0 to 20 parts by weight of at least one thixotrope.

* * * * *

UNITED STATES PATENT AND TRADEMARK OFFICE
CERTIFICATE OF CORRECTION

PATENT NO.: 5,587,502

DATED: Dec. 24, 1996

INVENTOR(S): Dean M. MOREN and Ian R. OWEN

It is certified that error appears in the above-identified patent and that said Letters Patent is hereby corrected as shown below:

Column 2, Line 46, "nonlo" should be --non-silane--;

Column 5, Line 51, "3aminopropylphenyldiethoxysilane" should be --3-aminopropylphenyldiethoxysilane--;

Column 5, Line 58, "3 aminopropyl" should be --3-aminopropyl--;

Column 12, Line 25, "2 propylene" should be --2-propylene--;

Column 13, Line 43,44, "29Si-NMR" should be --$^{29}$Si-NMR--;

Column 23, Line 1, "DisIon" should be --Dislon--;

Claim 2, Column 25, line 8, "from 1059 the" should be --from the--;

Claim 13, Column 26, line 9, "m is O," should be --m is 0,--

Signed and Sealed this

Sixteenth Day of June, 1998

*Attest:*

BRUCE LEHMAN

*Attesting Officer*   Commissioner of Patents and Trademarks